US011612516B2

(12) United States Patent
Puglisi

(10) Patent No.: US 11,612,516 B2
(45) Date of Patent: Mar. 28, 2023

(54) IMMERSIVE DISPLAY SYSTEM FOR EYE THERAPIES

(71) Applicant: TEC MED S.R.L. TECNOLOGIE MEDICHE, Rome (IT)

(72) Inventor: Luca Puglisi, Rome (IT)

(73) Assignee: TEC MED S.R.L. TECNOLOGIE MEDICHE, Rome (IT)

( * ) Notice: Subject to any disclaimer, the term of this patent is extended or adjusted under 35 U.S.C. 154(b) by 327 days.

(21) Appl. No.: 16/768,053

(22) PCT Filed: Nov. 15, 2018

(86) PCT No.: PCT/IB2018/058987
§ 371 (c)(1),
(2) Date: May 28, 2020

(87) PCT Pub. No.: WO2019/106472
PCT Pub. Date: Jun. 6, 2019

(65) Prior Publication Data
US 2021/0205126 A1 Jul. 8, 2021

(30) Foreign Application Priority Data

Nov. 30, 2017 (IT) .......................... 102017000137984

(51) Int. Cl.
*A61F 9/007* (2006.01)
*A61B 90/00* (2016.01)
(Continued)

(52) U.S. Cl.
CPC ............ *A61F 9/007* (2013.01); *A61B 3/0058* (2013.01); *A61B 3/132* (2013.01); *A61B 3/145* (2013.01);
(Continued)

(58) Field of Classification Search
CPC .............. A61B 90/20; A61B 2090/365; A61B 2090/367; A61B 90/361; A61B 3/0058;
(Continued)

(56) References Cited

U.S. PATENT DOCUMENTS

2013/0088414 A1 4/2013 Artsyukhovich et al.
2014/0081659 A1* 3/2014 Nawana ............... A61B 5/4833
705/3

(Continued)

FOREIGN PATENT DOCUMENTS

CN 106200982 A 12/2016
WO 2013/082387 A1 6/2013

OTHER PUBLICATIONS

International Preliminary Report on Patentability, dated Jun. 11, 2020, from corresponding PCT application No. PCT/IB2018/058987.

(Continued)

*Primary Examiner* — Brandi N Thomas
(74) *Attorney, Agent, or Firm* — Nixon & Vanderhye

(57) ABSTRACT

An immersive display system for eye therapies includes an ophthalmic microscope and: a double video camera, connected to a local network infrastructure; the double video camera oriented for filming the surgery operation; at least one computerized control unit, connected to the local network infrastructure, receiving images from the double video camera and processing them in a three-dimensional digital format; and at least one computerized controller, receiving the images processed by the computerized control unit. Also included is at least one helmet adapted to be worn on the head by the surgeon during the surgery operation, the helmet provided with a viewer arranged before the wearer's eyes, configured for three-dimensional image display, providing virtual reality content; the viewer allows the surgeon exclusive viewing of the three-dimensional images processed by (Continued)

the computerized control unit; the helmet being connected to the local network infrastructure to allow image reproduction in real time.

12 Claims, 1 Drawing Sheet

(51) Int. Cl.
*A61B 3/00* (2006.01)
*A61B 3/13* (2006.01)
*A61B 3/14* (2006.01)
*H04N 13/344* (2018.01)

(52) U.S. Cl.
CPC ...... *A61B 90/361* (2016.02); *A61B 2090/365* (2016.02); *A61B 2090/367* (2016.02); *H04N 13/344* (2018.05)

(58) Field of Classification Search
CPC ... A61B 3/132; A61B 3/145; A61B 2090/373; A61B 2090/502; A61B 34/20; A61B 90/30; A61B 90/37; A61B 1/00193; A61B 2017/00216; A61B 2090/368; A61B 2090/371; A61B 1/00009; A61B 1/000094; A61B 1/000095; A61B 1/00039; A61B 1/00042; A61B 1/0005; A61B 2034/2055; A61B 2034/2057; A61B 2090/309; A61B 2090/372; A61B 256/0487; A61B 2576/00; A61B 3/107; A61B 3/113; A61B 3/13; A61B 5/0064; A61B 5/0066; A61B 5/0077; A61B 5/0086; A61B 5/1113; A61B 5/1114; A61B 5/1128; A61B 5/748; A61B 50/28; A61B 6/06; A61B 6/467; A61B 6/54; A61B 6/544; A61B 90/35; A61B 2017/00106; A61B 2017/00203; A61B 2017/00221; A61B 2034/102; A61B 2034/2065; A61B 2034/2068; A61B 2090/378; A61B 2090/3945; A61B 34/10; A61B 34/25; A61B 90/36; G02B 21/22; G02B 27/017; G02B 2027/0138; G02B 2027/014; G02B 2027/0187; G02B 27/0172; G02B 2027/0134; G02B 2027/0141; G02B 2027/0147; G02B 27/0093; G02B 27/0101; G02B 7/1822; G02B 2027/0178; G02B 23/2415; G02B 30/25; H04N 13/344; H04N 13/239; H04N 13/122; H04N 13/167; H04N 13/189; H04N 13/211; H04N 13/246; H04N 13/254; H04N 13/257; H04N 13/286; H04N 13/296; H04N 13/337; H04N 13/341; H04N 13/366
See application file for complete search history.

(56) References Cited

U.S. PATENT DOCUMENTS

| 2016/0095514 A1* | 4/2016 | Meckes | A61B 3/102 351/208 |
|---|---|---|---|
| 2017/0143442 A1 | 5/2017 | Tesar et al. | |
| 2017/0273549 A1 | 9/2017 | Nazareth et al. | |

OTHER PUBLICATIONS

International Search Report, dated Feb. 22, 2019, from corresponding PCT application No. PCT/IB2018/058987.
Written Opinion, dated Feb. 22, 2019, from corresponding PCT application No. PCT/IB2018/058987.

* cited by examiner

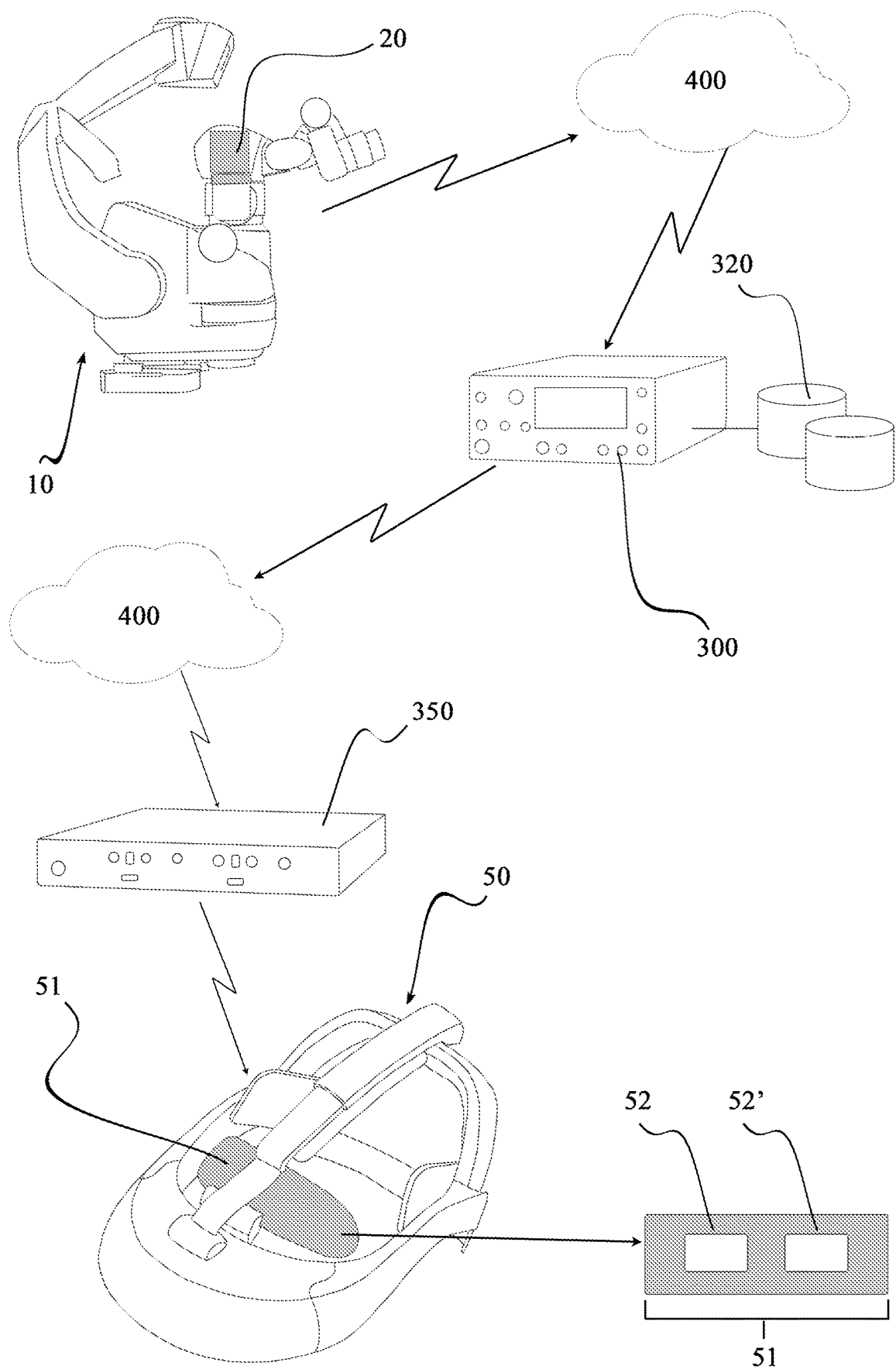

IMMERSIVE DISPLAY SYSTEM FOR EYE THERAPIES

FIELD OF THE ART

The present invention operates in the field of viewing technologies in a manner known with the name "virtual reality". More in detail, the object of this patent application is a virtual reality viewing system applied to eye surgery.

PRIOR ART

Conventionally, in eye surgery, ophthalmic microscopes are used which allow the surgeon to have a detailed view of the eye during operation. The most modern models of such microscopes are provided with a monitor, also large-size and very-high definition, on which the images filmed by the microscope are reported in real time.

This implementation of the microscopes is aimed to allow the surgeon to operate while examining the monitor and hence with his/her head up, contrary to what was necessary with the old microscopes, which obliged him/her to be in a curved position and to suffer vision fatigue.

Microscopes provided with 3D screen are also present on the market, which are associated with suitable polarized glasses that the doctor must wear during the operation in order to use the technology for viewing the three-dimensional images.

It is clear that the technology of the surgery field is oriented towards facilitating the work of the doctor who, during the operation, must maintain the greatest possible concentration without tiring. And this without giving up the quality of the image reproduced with video, of fundamental importance above all for a refined surgery field like that of eye surgery.

For the grounds just set forth above, 3D screen technology does not help the surgeon who, in order to make more realistic use of the images, is obliged to make continuous adjustments of the glasses and suffers considerable eye fatigue. The bulk of the screens is also to be considered: usually 50 inches, which is poorly adaptable to small operating rooms.

Also the screen display, even if improved with respect to that in the microscope, obliges the doctor to be in an unnatural position, as he/she must look to the side, which in the long term can be more tiring than a front display.

A further problem regarding eye operations this time regards the patient. The ophthalmic microscopes currently available on the market are in fact provided with a light that can have a phototoxic effect and lead to maculopathies. The prolonged exposure of the eye to such light sources and the possible use of intraocular optical fibers can even lead to irreversible damage.

The object of some international patents pertains to medical surgery systems based on virtual reality technology, which in recent years has developed considerably. One example thereof is the Chinese patent CN 106 200 982 which describes a system comprising a helmet for virtual reality and a sensitive glove that sends data to a computer. A virtual reality software is incorporated in the computer and is used for collecting actual human body data and reporting it in a three-dimensional virtual model of the treated human body. The technical problem that one intends to resolve with the object of this patent is correlated with the teaching of surgery techniques to students.

The object attained by the object of the present patent application is very different. It specifically regards the eye surgery field and has therapeutic, not didactic application. Due to the system described in more detail hereinbelow, the risk of damage to the patient's eyesight will be eliminated, and the doctor will be assisted in operating in a precise manner and without tiring due to the complete immersion in the scene of the operation, by exploiting the most modern technologies of augmented reality, and additionally protecting the surgeon himself/herself from the continuous exposure of the return light towards the eyes.

DESCRIPTION OF THE INVENTION

According to the present invention, a hardware-software integrated system is attained which effectively resolves the abovementioned problems.

In addition to the conventional ophthalmic microscope whose use is already widely known in the ophthalmological field, the present system comprises at least:

a double video camera;
a computerized control unit;
a helmet with viewer for virtual reality;
a computerized controller;
a local network infrastructure.

Said double video camera is advantageously installed on the ophthalmic microscope so as to film the scene of the surgery operation in a continuous manner Due to the connection to the local network, by means of any one wired or wireless technology, the images are transmitted in real time to said computerized control unit. By using a virtual reality software, the images are processed and transmitted, due to a wired or wireless network infrastructure, in real time, to said computerized controller which sends them at least to the viewer of the helmet worn by the operating surgeon and possibly also to other helmets which for example can be worn by the interns.

Such helmet is constituted by a so-called "head mount display" and it is configured for providing the surgeon with an image viewing experience that is completely immersive, according to the dictates of the nascent science of "virtual reality".

In a preferred embodiment, within the viewer of the helmet, two displays are present, which once the helmet is put on the head are arranged as follows: one at the left eye and one at the right eye of the surgeon.

Possibly and preferably, the viewer can be provided with a zoom system and/or with a key to be pressed in order to take photographs during the operation.

Advantageously, said computerized control unit acts as a communications interface with a user or with the surgeon himself/herself. Even if said computerized control unit is adapted to automatically govern the settings of the double video camera with regard to color, exposure, brightness, contrast, etc. . . . , such settings can advantageously be set, before the start of the operation, by the surgeon who sets the operating parameters of the double video camera and of the viewer according to his/her own preferences.

A further advantageous embodiment comprises a memory in which all the images filmed by the double video camera are recorded, in three-dimensional digital format, and saved in association with the name of the patient and/or with the name of the surgeon who executed the operation.

It is clear that the present invention entirely eliminates the eye fatigue for the surgeon during the operation, without compromising the image use/experience which is not only of optimal quality, but also is immersive for the observer who is situated at the center of the scene of the operation, without the possibility of being distracted.

Due to the improved use of the images, some surgery operations, such as for example those which affect the anterior segment, can be executed without using coaxial light, with the consequent cancelation of the side effects for the patient due to an excessive and prolonged exposure to light.

The advantages offered by the present invention are evident in light of the description set forth up to now and will be even clearer due to the enclosed FIGURES and to the relative Detailed Description.

DESCRIPTION OF THE FIGURES

The invention will be described hereinbelow in at least one preferred embodiment, by way of a non-limiting example with the aid of the enclosed FIGURES in which:

FIG. 1 shows a block diagram of the interrelations between the components of the system of the present invention. Due to the network infrastructure 400, the images filmed by double video camera 20 installed on the ophthalmic microscope 10 are sent to a computerized control unit 300, connected to a memory 320, which sends them in digital form to the computerized controller 350 and from here to the viewer 51 of the helmet 50 worn by the surgeon. In said viewer 51, a left display 52 and a right display 52' cooperate for the delivery of three-dimensional images perceived by the observed in completely immersive form.

DETAILED DESCRIPTION OF THE INVENTION

The present invention will now be illustrated as a merely non-limiting, non-binding example, with reference to the FIGURES which illustrate several embodiments relative to the present inventive concept.

With reference to FIG. 1, all the technological components are shown which, due to their interaction, enable the virtual reality viewing of the scene of the surgery operation by the doctor who is executing the operation and possibly also by other users present at the operation.

In addition to the ophthalmic microscope 10 which is already known and present in every operating room of the field, there is also a double video camera 20 suitable for the reproduction of the images in three-dimensional digital format. Said double video camera 20, due to a local network infrastructure 400, wired or wireless, sends the filmed images to a computerized control unit 300 which transmits them to the viewer 51 of a helmet 50 worn by the surgeon.

Such viewer 50 is a "head mount display" for displaying digital contents of augmented reality which, in this case, consist of the complete immersion in the scene of the surgery operation that is being executed in real time.

Still in the reference FIGURE, one sees that the interior of the viewer 51, i.e. the part that covers the eyes of the helmet 50 wearer, in this case the surgeon, is organized with a left display 52 and a right display 52' which come to be automatically positioned in front of the left eye and right eye of the surgeon when he/she puts on the helmet 50.

Possibly, the helmet 50 can be provided with keys or other technological systems for executing the zoom as desired by the surgeon and/or the freeze-frame to be saved in the memory 320 of the computerized control unit 300 for a future analysis of the operation.

The computerized control unit 300 processes a flow of images for the left screen 52 and a flow of images for the right screen 52', ensuring that when combined the vision of the surgeon will be as natural as possible, making him/her feel that he/she is at the center of the scene of the operation, independent of the position of the head and the direction of his/her glance/look, since one such image reproduction form is completely immersive.

The computerized control unit 300, in the preferred embodiment, can be connected to a memory 320 in which all the images filmed by the double video camera 20 are saved, associating them both with the name of the operated patient and the name of the surgeon.

In a further preferred embodiment, the settings of the double video camera 20 and of the viewer 51 of the helmet 50 are settable before starting the operation according to the preferences of the surgeon, due to the computerized control unit 300.

Due to said network infrastructure 400 that can be either wired or wireless, the images are sent to a computerized controller 350 which manages the transmission thereof to the helmet 50 of the surgeon and to possible further helmets 50 of observers connected to the system.

Finally, it is clear that modifications, additions or variants can be made to the invention described up to now that are obvious for a man skilled in the art, without departing from the protective scope that is provided by the enclosed claims.

The invention claimed is:

1. An immersive display system for eye therapies, adapted to provide a surgeon with a three-dimensional image of ocular tissues during an ophthalmological surgery operation using an ophthalmic microscope (10), the immersive display system comprising:

a double video camera (20), installed on said ophthalmic microscope (10) and connected to a local network infrastructure (400), said double video camera (20) being oriented so as to continuously capture images of a scene of the surgery operation;

at least one computerized control unit (300), connected to at least one memory (320) and connected to said local network infrastructure (400), said computerized control unit (300) adapted to receive the images captured by said double video camera (20) and to process the images into a three-dimensional digital format, said computerized control unit (300) being adapted to automatically manage operative settings of said double video camera (20) for at least one of brightness, color, exposure and contrast;

a computerized controller (350), connected to said local network infrastructure (400) and adapted to receive the images processed by said computerized control unit (300); and a helmet (50), adapted to be worn on the head by the surgeon during the surgery operation, said helmet (50) being provided with a viewer (51) that is adapted to be arranged in front of the eyes of the surgeon when the helmet is worn by the surgeon, the viewer configured to present the surgeon with a three-dimensional image display, and the helmet (50) being connected to said local network infrastructure (400), the computerized controller (350) adapted to send the images processed by the computerized control unit (300) to the helmet (50) via the local network infrastructure, said helmet (50) configured to receive the images via the local network infrastructure so as to allow reproduction of the images by means of said viewer (51) in real time, said viewer (51) configured to provide the surgeon exclusive viewing of the three-dimensional images processed by said computerized control unit (300) and received from said computerized controller (350), and comprising a left display (52) and a right display (52') respectively arranged to be located in front of the left eye and in front of the right eye of the surgeon wearing the helmet, said left and right displays cooperating to provide the surgeon with the reproduction of the images in a three-dimensional display mode, wherein the images of the surgery operation are saved in said memory (320) together with information associating the images with the name of the patient, and wherein the images of the surgery operation are saved in said memory (320) together with information associating the images with the name of the surgeon who executes the surgery operation.

2. The immersive display system for eye therapies according to claim 1, wherein said computerized control unit (300) is configured to allow said surgeon to set operating parameters of said double video camera (20) and of said viewer (51).

3. The immersive display system for eye therapies according to claim 1, wherein said computerized control unit (300) is adapted to record in the memory (320) all the images captured by said double video camera (20) in a three-dimensional digital format.

4. The immersive display system for eye therapies according to claim 1, wherein said viewer (51) is provided with a zoom system that allows the surgeon to enlarge a detail or a particular area of the surgery operation.

5. The immersive display system for eye therapies according to claim 1, wherein said viewer (51) is provided with a capture system for capturing the images as photographs to allow the surgeon to capture freeze-frames of the images during the surgery operation.

6. The immersive display system for eye therapies according to claim 2, wherein said computerized control unit (300) is adapted to record in the memory (320) all the images captured by said double video camera (20) in a three-dimensional digital format.

7. The immersive display system for eye therapies according to claim 2, wherein said viewer (51) is provided with a zoom system that allows the surgeon to enlarge a detail or a particular area of the surgery operation.

8. The immersive display system for eye therapies according to claim 3, wherein said viewer (51) is provided with a zoom system that allows the surgeon to enlarge a detail or a particular area of the surgery operation.

9. The immersive display system for eye therapies according to claim 2, wherein said viewer (51) is provided with a capture system for capturing the images as photographs to allow the surgeon to capture freeze-frames of the images during the surgery operation.

10. The immersive display system for eye therapies according to claim 3, wherein said viewer (51) is provided with a capture system for capturing the images as photographs to allow the surgeon to capture freeze-frames of the images during the surgery operation.

11. The immersive display system for eye therapies according to claim 4, wherein said helmet (50) is provided with keys for executing the zoom system for enlarging the detail or the particular area of the surgery operation.

12. The immersive display system for eye therapies according to claim 5, wherein said helmet (50) is provided with keys for executing the capture system for capturing one or more of the images during the operation as a freeze-frame.

* * * * *